US009283206B2

(12) United States Patent
Cabrini et al.

(10) Patent No.: US 9,283,206 B2
(45) Date of Patent: Mar. 15, 2016

(54) TRIMETHYLANGELICIN AS CFTR CORRECTOR IN BRONCHIAL EPITHELIAL CELLS

(75) Inventors: Giulio Cabrini, Verona (IT); Valeria Casavola, Bari (IT); Roberto Gambari, Ferrara (IT)

(73) Assignees: Azienda Ospedaliera Universitaria Integrata di Verona, Verona (IT); Universita' degli Studi di Ferrara, Ferrara (IT); Universita' degli Studi di Bari, Bari (IT); Rare Partners S.r.l., Milan (IT)

( * ) Notice: Subject to any disclaimer, the term of this patent is extended or adjusted under 35 U.S.C. 154(b) by 158 days.

(21) Appl. No.: 14/125,109

(22) PCT Filed: Jun. 13, 2012

(86) PCT No.: PCT/EP2012/061193

§ 371 (c)(1), (2), (4) Date: Jan. 15, 2014

(87) PCT Pub. No.: WO2012/171954

PCT Pub. Date: Dec. 20, 2012

(65) Prior Publication Data

US 2015/0290167 A1 Oct. 15, 2015

(30) Foreign Application Priority Data

Jun. 14, 2011 (IT) .................................. M111A1068

(51) Int. Cl.

| | |
|---|---|
| ***A61K 31/366*** | (2006.01) |
| ***A61K 31/37*** | (2006.01) |
| ***A61K 31/443*** | (2006.01) |
| ***A61K 31/47*** | (2006.01) |

(52) U.S. Cl.

CPC ............... *A61K 31/366* (2013.01); *A61K 31/37* (2013.01); *A61K 31/443* (2013.01); *A61K 31/47* (2013.01)

(58) Field of Classification Search

CPC .................................................. A61K 31/366
USPC .......................................... 549/282; 514/455
See application file for complete search history.

(56) References Cited

U.S. PATENT DOCUMENTS 7,572,827 B2 * 8/2009 Bianchi .................. A61K 31/37 514/453

OTHER PUBLICATIONS

Anna Tamanini, et al., Trimethylangelicin Reduces . . . , American Journal of Physiology Lung Cellular and Molecular Physiology, vol. 300, No. 3, 2010, XP008140643.
Fredrick Van Goor, et al., VX-809, A CFTR Corrector, Increases the Cell . . . , Pediatric Pulmonology; 23rd Annual North American Cystic Fibrosis Conference, vol. 44, No. suppl. 32, 2009, XP008140853.
Fredrick Van Goor, et al., Rescue of CF Airway Epithelial Cell . . . , PNAS. vol. 106, No. 44, 2009, XP002680867.
Study of VX-809 in Cystic Fibrosis with the F508-CFTR Gene Mutation, 2011, XP002680868.
Study of VX-770 in Cystic Fibrosis Subjects Age 12 and Older . . . , 2011, XP002680869.
Study of VX-809 Alone and in Combination with VX-770 in cystic Fibrosis . . ., 2011, XP002680870.
International Search Report issued in counterpart PCT Application No. PCT/EP2012/061193.
Written Opinion of International Searching Authority issued in counterpart PCT Application No. PCT/EP2012/061193.

* cited by examiner

*Primary Examiner* — Golam M M Shameem

(74) *Attorney, Agent, or Firm* — Silvia Salvadori, PC.; Silvia Salvadori

(57) ABSTRACT

The invention relates to the use of 4,6,4'-trimethylangelicin (TMA) and structural analogs thereof to prepare a medicament for the treatment of cystic fibrosis with the primary objective of correcting the defective CFTR in a sub-group of cystic fibrosis patients consisting of patients carrying the F508del-CFTR mutation.

2 Claims, 4 Drawing Sheets

FIGURE 1. Concentration response of F508del CFTR-dependent chloride efflux to TMA and VX809 in CFBE41o- monolayers.
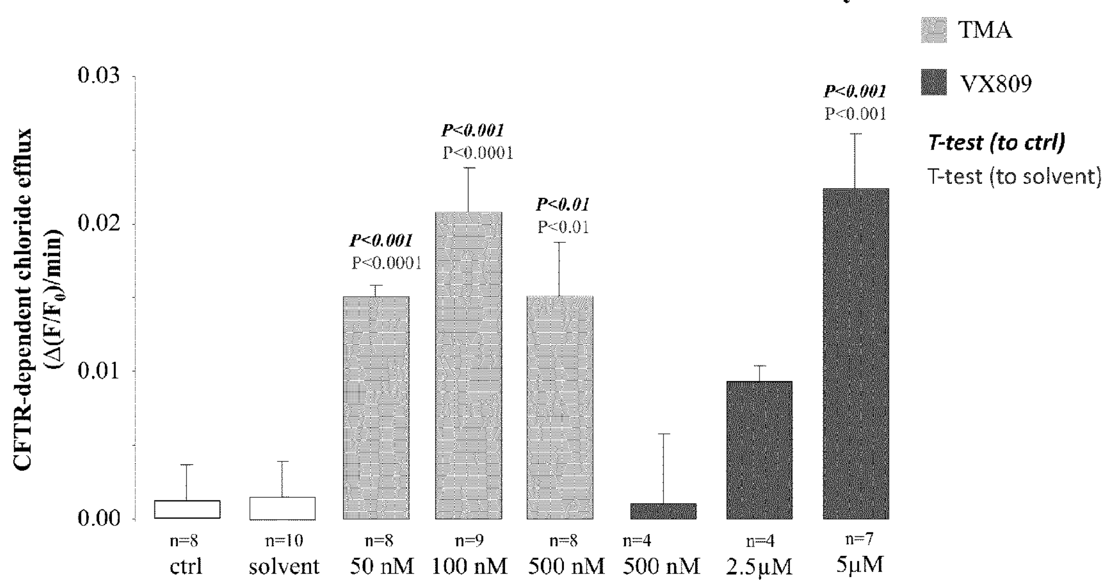

FIGURE 2. Effect of TMA and VX809 treatment on apical membrane F508del CFTR expression in CFBE41o⁻ polarized monolayers
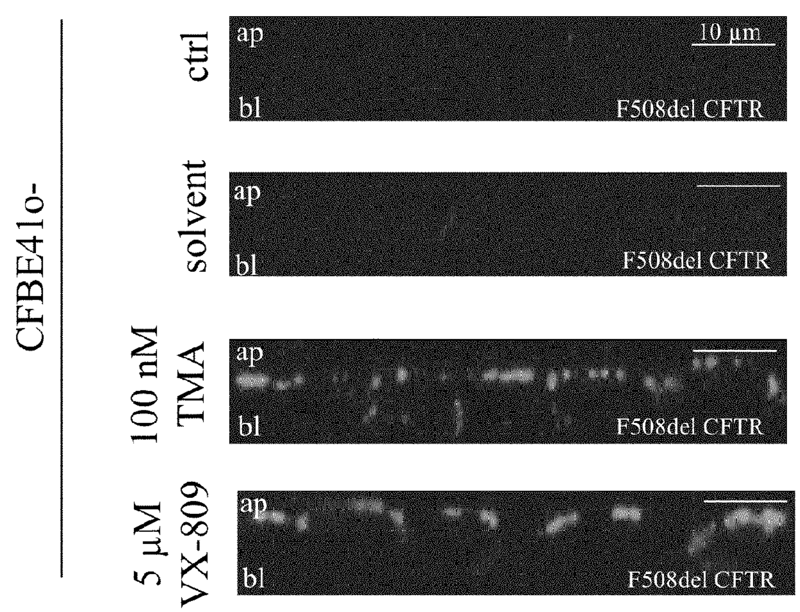

FIGURE 3. Effect of TMA treatment on F508del CFTR functional expression in CuFi-1 cells.
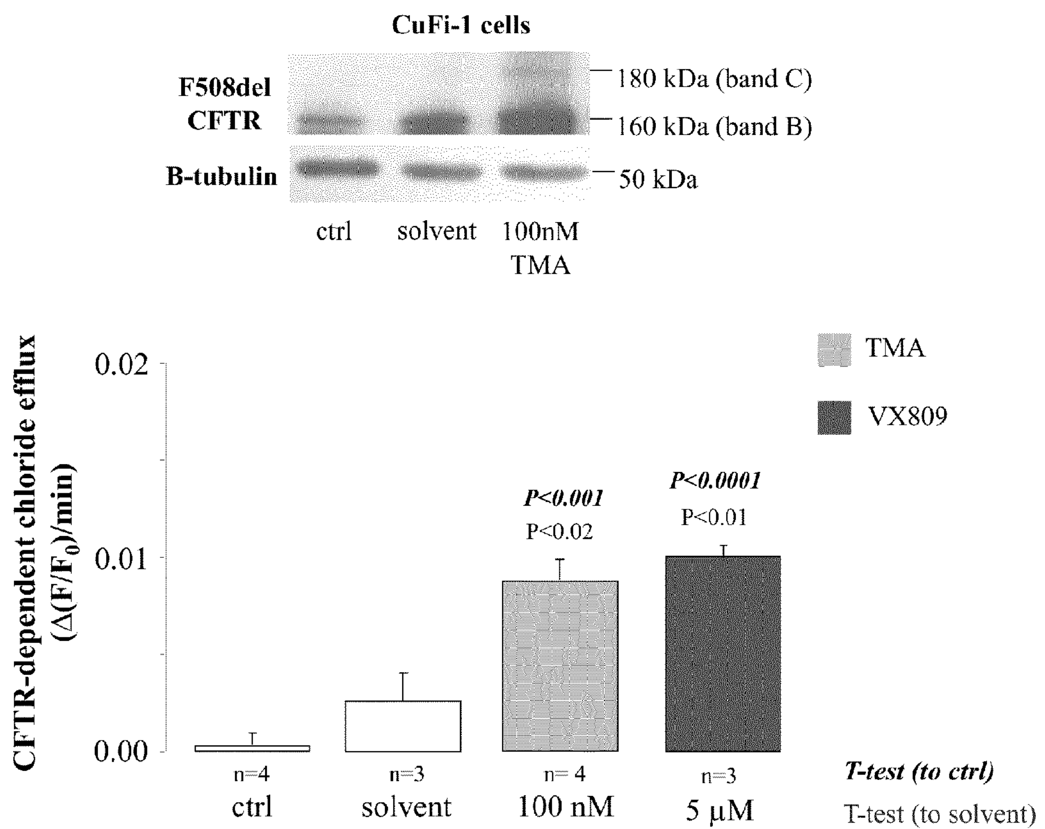

FIGURE 4. Effect of TMA treatment on apical membrane F508del CFTR expression and activity in primary MucilAir-CF cell monolayers.
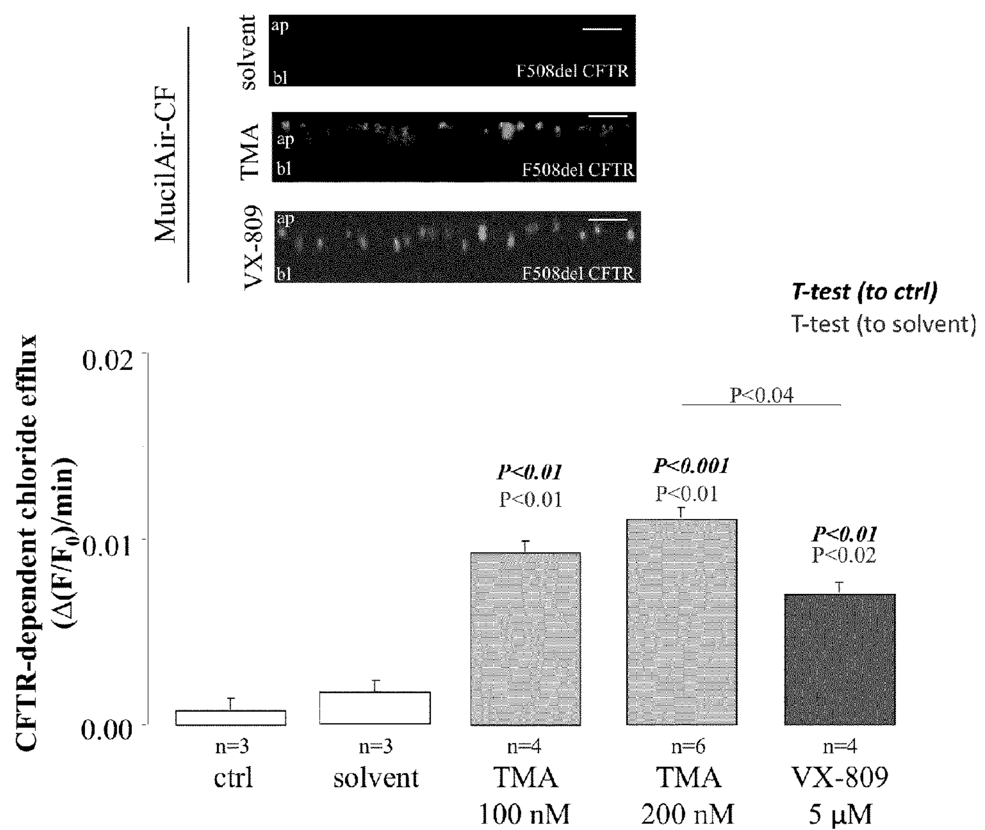

TRIMETHYLANGELICIN AS CFTR CORRECTOR IN BRONCHIAL EPITHELIAL CELLS

This application is a U.S. national stage of PCT/EP2012/061193 filed on Jun. 13, 2012, which claims priority to and the benefit of Italian Application No. MI2011A001068 filed on Jun. 14, 2011, the contents of which are incorporated herein by reference in their entirety.

DESCRIPTION

The present invention relates to the use of an angular psoralen, trimethylangelicin (4,6,4'-trimethylangelicin—TMA), a molecule able to correct the intracellular localisation of the membrane protein called CFTR (Cystic Fibrosis Transmembrane conductance Regulator) carrying the F508del CFTR mutation, which is altered in a sub-group of patients suffering from cystic fibrosis. Said molecule is proposed for the preparation of a medicament for the treatment of cystic fibrosis (CF) in the sub-group of patients characterised by the F508del mutation of the CFTR gene.

PRIOR ART

Cystic fibrosis is an autosomal recessive genetic disorder caused by mutations of the gene encoding for CFTR. The incidence of the disease among the Caucasian population is 1/2000-3000 newborns, whereas it is much lower among native Africans and Asians (1). Over 1,500 mutations of the CFTR gene have been identified, involving 5 classes of molecular defects of the protein (Class I: complete absence of CFTR protein synthesis; Class II: arrested maturation and intracellular localisation defect of the CFTR protein; Class III: inhibition of regulation with defective activation of the chloride ion transport function; Class IV: reduced conductance of the chloride ion; Class V: reduced CFTR protein synthesis). The most common mutation of the CFTR gene is deletion of phenylalanine in position 508 of the polypeptide chain (mutation F508del-CFTR), which involves a Class II defect (1). The main molecular defect of the F508del-CFTR protein therefore relates to the non-localisation of the protein on the apical membrane of the epithelial cells involved in the organic disease cystic fibrosis (1). In addition, when the F508del-CFTR protein can be corrected for its cell localisation defect by experimental manipulations, it also shows reduced conductance of the chloride ion compared with normal CFTR protein, an additional defect that suggests the need to also enhance this reduced function (1). All the molecular defects described for the CFTR protein therefore involve complete absence of chloride ion transport arising from different mechanisms (severe mutations for Class I, II and III defects), or at any rate a significant reduction which expresses the disease (mild mutations for Class IV and V defects). A reduced or absent chloride ion transport function causes disease in various tissues, but the respiratory tract is the most critical organ in reducing the duration and quality of life of patients suffering from cystic fibrosis. In particular, in the respiratory tract, the various molecular defects of the CFTR protein and, consequently, its reduced or absent chloride ion transport function, lead to chronic bacterial infections and the onset of a chronic inflammatory state, which cause progressive lung damage and respiratory failure.

For these reasons, the discovery of molecules able to correct and/or enhance CFTR, combat multiresistant bacterial strains and reduce excessive pulmonary inflammation is very important in the development of innovative treatments for cystic fibrosis (2). At present, the treatment of lung disorders in cystic fibrosis requires the development of innovative drugs aimed at the concomitant aspects of the disease and, consequently, modulators of the defective CFTR protein, new antibacterials and new anti-inflammatories, which can be used in parallel to perform a synergic action (2). As regards modulators of the defective CFTR protein, two distinct classes of molecules are under study, called “potentiators” and “correctors”, depending on the class of molecular defect of the CFTR protein, determined by the specific mutation of the CFTR gene (3). In this respect, pulmonary treatment of cystic fibrosis will require concomitant drugs with differentiated actions, due to the multiple mechanisms of lung damage (chloride transport defect, bacterial infection and chronic inflammation) and to the different classes of molecular defect of the CFTR protein and gene which are expressed in patients suffering from cystic fibrosis (3). For example, VX-770, an innovative medicament with the function of “potentiator” of CFTR protein with a Class III defect, is successful only in patients suffering from cystic fibrosis with the G551D-CFTR gene defect, who represent 1-5% of all the cystic fibrosis patients (4-5), but has no significant therapeutic efficacy in patients who are homozygous for the F508del-CFTR mutation (6), confirming the need for customised treatments for sub-groups of patients suffering from cystic fibrosis depending on the mutations of the CFTR gene and the CFTR protein molecular defect class. For patients with the F508del-CFTR mutation, new molecules with the function of “correctors” of the mutated CFTR protein are under study; the VX-809 molecule is at the most advanced stage. VX-809 has been experimentally characterised in cell models in vitro (7) and then directly in phase IIa clinical trials on patients suffering from cystic fibrosis (8). As the mutated protein F508del-CFTR, in addition to the Class II defect (arrested maturation and intracellular localisation defect of the CFTR protein) also presents reduced chloride ion conductance, clinical trials are in progress where the VX-809 “corrector” is associated with the VX-770 “potentiator” to modulate the function of the mutated protein F508del-CFTR as efficiently as possible (9). Briefly, the treatment of cystic fibrosis patients requires different modulators of the mutated CFTR protein, namely “correctors” and/or “potentiators”, depending on the mutations of the CFTR gene, which divide the patients into genetically distinct sub-groups, and complementary medicaments with an antibacterial action and an anti-inflammatory action.

We have previously demonstrated that an angelicin analogue, 4,6,4'-trimethylangelicin (TMA), is a powerful inhibitor of the inflammatory process induced in cystic fibrosis cells by *P. aeruginosa* infection and a potent “potentiator” of F508del-CFTR (10). An interesting finding is that its anti-inflammatory activity is considerably greater than that of other psoralens currently used in the clinical treatment of chronic inflammatory skin disorders, such as 5-methoxypsoralen (5-MOP) and 8-methoxypsoralen (8-MOP) (10). The possible anti-inflammatory action mechanism is suggested by the interaction of 4,6,4'-trimethylangelicin with the nuclear transcription factor NF-kB, which is known to play a key role in inflammatory processes (10). The interaction of 4,6,4'-trimethylangelicin with NF-kB was suggested by the findings of earlier in silico studies with similar, but not identical molecules, such as 4,5',4'-trimethylangelicin (11).

BRIEF DESCRIPTION OF THE DRAWINGS

FIG. 1 shows the effect of TMA in CFBE41o- polarized monolayers.

FIG. 2 shows confocal scans in the vertical cross-section (xz) planes.

FIG. 3 shows a representative Western blot of a typical experiment.

FIG. 4 shows the effect of TMA as a corrector in primary bronchial epithelial cells.

DESCRIPTION OF THE INVENTION

We have discovered that 4,6,4'-trimethylangelicin (TMA) is a powerful "corrector" of F508del-CFTR. This effect is unexpected, and has not been previously described for linear and angular psoralens, which have been studied for decades, including on cystic fibrosis cells. The same molecule (TMA), therefore, possesses three activities, all of which are of interest for the treatment of cystic fibrosis: anti-inflammatory activity, F508del-CFTR "potentiator" activity and F508del-CFTR "corrector" activity.

The structural formula of TMA, compared with angelicin and with the compound 8-MOP and 5-MOP (selected by way of example from the linear psoralens), is as follows:

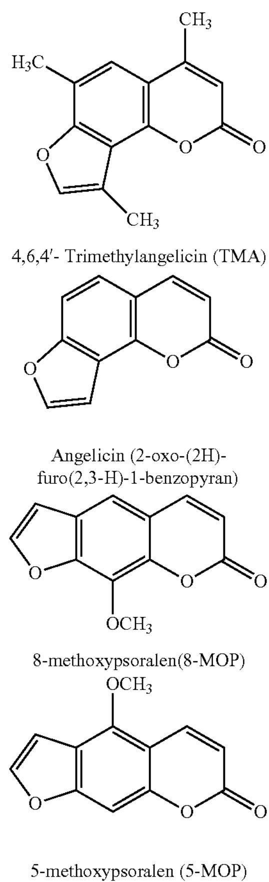

4,6,4'- Trimethylangelicin (TMA)

Angelicin (2-oxo-(2H)-furo(2,3-H)-1-benzopyran)

8-methoxypsoralen(8-MOP)

5-methoxypsoralen (5-MOP)

Earlier results demonstrated that TMA inhibits the accumulation of IL-8 mRNA in bronchial epithelial cells IB3-1 (12) after infection with *P. aeruginosa* (10) and, in parallel, that it possesses an effect as "potentiator" on F508del-CFTR.

The activity of 4,6,4'-TMA as "corrector" of F508del-CFTR, which underlies the invention, is unexpected in view of the known therapeutic uses of structural analogues of 4,6,4'-TMA (13-24).

The chemical synthesis of 4,6,4'-TMA, and of the psoralens in general, has been described by various research groups (see, for example, references 15-18).

A first subject of the present invention is therefore 4,6,4'-trimethylangelicin for use as a "corrector" of F508del-CFTR either in heterozygous or homozygous state in patients suffering from cystic fibrosis.

Moreover, a combined treatment with various modulators of the mutated protein F508del-CFTR could increase the biological and clinical response to the treatment.

A second subject of the present invention is therefore a combination of 4,6,4'-trimethylangelicin (TMA) with at least one further molecule with a modulating action such as another "corrector" or "potentiator" of mutated CFTR, such as the corrector 3-{6-{[1-(2,2-difluoro-1,3-benzodioxol-5-yl)cyclopropanecarbonyl]amino}-3-methylpyridin-2-yl} benzoic acid (VX-809) and the "potentiator" N-(2,4-di-tert-butyl-5-hydroxyphenyl)4-oxo-1,4-dihydroquinoline-3-carboxamide (VX-770).

TMA can be administered by suitable delivery systems, to facilitate the correcting/enhancing effect on F508del-CFTR compared with the anti-inflammatory effect, depending on the patient's genotype/phenotype. TMA, either alone or combined with said medicaments, can be administered orally or by inhaler; examples of formulations suitable for oral administration include capsules, tablets, syrups, solutions or drinkable suspensions and similar conventional dosage forms. Dosage forms suitable for administration by inhaler include solutions, suspensions or powders to be administered with the aid of conventional devices such as MDIs (metered dose inhalers), possibly using suitable gaseous carriers such as HFA.

The TMA doses can be determined by experts in the field on the basis of pharmacodynamic and pharmacokinetic tests, and will also depend on the weight, age and condition of the patient and on other parameters which will be determined by the patient's doctor. Broadly speaking, the effective doses can range from approx. 10 to approx. 500 mg, preferably from approx. 10 to approx. 250 mg of TMA a day, possibly divided into a number of administrations, although lower or higher doses cannot be ruled out.

The activity of TMA as a corrector of F508del-CFTR was demonstrated by evaluating the CFTR-dependent chloride efflux in polarised cell monolayers, measured by spectrofluorimetry. The use of monoclonal antibodies for CFTR has also highlighted the correction of the intracellular localisation, bringing the mutated CFTR protein onto the plasma membrane, and the expression of biochemically mature F508del-CFTR protein.

The invention is illustrated in greater detail in the following examples.

EXAMPLE 1

Functional correction of F508del-CFTR was assessed by analysing the changes in intracellular CF-dependent MQAE fluorescence (expressed as the $F/F_0$ ratio) in human bronchial epithelial cells expressing mutated F508del-CFTR protein, grown as polarised cell monolayers on permeable filters, as extensively described previously (25-26). Cells were pretreated or not with the TMA or the VX-809 compounds for 24 hrs, then treated for 3 min with 10 μM FSK plus 100 μM IBMX before substitution of apical chloride by nitrate first in the absence and then in the presence of the specific CFTR inhibitor 5 μM $CFTR_{inh}$-172(27). $CFTR_{inh}$-172 is added apically 5 min before nitrate substitution and remained for the entire efflux. FIG. 1 reports the effect of TMA in $CFBE41o^-$ polarised monolayers, an immortalised cell line derived from a patient affected by cystic fibrosis carrying the mutated F508del-CFTR protein, grown on permeable filters. Cells were treated for 24 hrs with increasing concentrations of TMA from 50 nM to 500 nM (grey bars), or from 500 nM to 5 μM of VX809 (black bars). CFTR-dependent chloride transport was calculated from the difference in alterations of FSK+IBMX-stimulated fluorescence measurements in the absence and presence of the CFTR inhibitor, CFTRinh-172 (5 μM). Each bar represents the mean±S.E.M. for the calculated differences. Statistical comparisons were made using an unpaired Student's t test with respect to the values obtained in untreated monolayers (ctrl) or in monolayers treated only with the solvent. This example demonstrates that TMA is a corrector of the functional defect of mutated F508del-CFTR protein in human bronchial epithelial cells. The comparison of TMA with the VX-809 corrector indicates that TMA obtains a similar effectiveness but at much lower concentrations than those required for the VX-809 compound (100 nM for TMA versus 5 mM for VX-809).

EXAMPLE 2

The above findings that TMA is a functional corrector of the mutated F508del-CFTR protein, was checked and extended by assessing the effect of TMA on the intracellular localisation of the mutated protein in the same CFBE41o$^-$ monolayers at the end of the functional assay described in FIG. 1, by confocal immunofluorescence microscopy images of polarised CFBE41o$^-$ monolayers grown on permeable filters, treated or not with TMA (100 nM) or VX809 (5 μM) for 24 hrs. Unpermeabilised cells were immunolabelled with a primary mouse monoclonal antibody (CF3) raised against the extracellular first loop of CFTR (26). FIG. 2 shows confocal scans in the vertical cross-section (xz) planes. In untreated cells (ctrl) or treated with solvent, F508del CFTR was not expressed in the apical membrane, whereas after 100 nM TMA or 5 μM VX809 treatment, F508del CFTR was significantly translocated to the apical membrane (ap, location of apical membrane; bl, location of basolateral region. Scale bar, 10 μm).

EXAMPLE 3

The validation of the effect of F508del CFTR protein correctors, such as VX-809, before applying the molecules in human clinical trials, is not usually performed in pre-clinical in vivo models, such as in murine strains, but should be carried out by testing more than a single bronchial epithelial cell line expressing the mutated protein in vitro (7, 28). TMA was therefore tested as a F508del CFTR protein corrector in the immortalised CuFi-1 cell line, which derives from a cystic fibrosis patient carrying the mutated F508del CFTR protein. Expression levels of F508del CFTR were analyzed in CuFi-1 cells before and after incubation with TMA (100 nM) for 24 hrs by Western blotting using anti-hCFTR antibody. FIG. 3 shows a representative Western blot of a typical experiment. The blot shows that in the cells treated with TMA (100 nM), there is an increase in the levels of F508del CFTR protein, particularly evident in the mature form of CFTR. Monolayers of CuFi-1 cells, grown on permeable filters, were treated with TMA (100 nM) or with VX809 (5 μM) for 24 hrs and the CFTR-dependent chloride transport was determined. The chloride transport was calculated from the difference in alterations of FSK-stimulated fluorescence measurements in the absence and presence of the CFTR inhibitor, CFTRinh-172. Each bar represents the mean±S.E.M. for the calculated differences. Statistical comparisons were made using an unpaired Student's t test with respect to the values obtained in untreated monolayers or in monolayers treated only with the solvent. Example 3 gives further strong support for the effect of TMA as corrector of mutated F508del CFTR protein.

EXAMPLE 4

A further level of pre-clinical validation of mutated F508del CFTR protein correctors was obtained by testing the candidate molecule in primary bronchial epithelial cells obtained from the lungs of cystic fibrosis patients without the genetic manipulation inherent in cell immortalisation. These experiments were performed because as it has been demonstrated that F508del CFTR protein correctors could be effective in immortalised cell lines but not in the real cellular target, which is most closely represented by the model of the primary bronchial epithelial cells in vitro (29). The results reported in FIG. 4 show the effect of TMA as a corrector in primary bronchial epithelial cells from a cystic fibrosis patient carrying the mutated F508del CFTR protein, grown as monolayers on permeable filters in air-liquid interface (MucilAir-CF cells). Primary cells were treated for 24 hrs with 100 nM or 200 nM TMA. CFTR-dependent chloride transport was calculated from the difference in alterations of FSK+IBMX-stimulated fluorescence measurements in the absence and presence of the CFTR inhibitor, CFTRinh-172 (5 μM). Each bar represents the mean±S.E.M. for the calculated differences. Statistical comparisons were made using an unpaired Student's t test with respect to the values obtained in untreated monolayers (ctrl) or in monolayers treated only with the solvent. After the functional experiments, cells were fixed and immunolabelled with a primary mouse monoclonal antibody (CF3) raised against the extracellular first loop of CFTR. Confocal immunofluorescence microscopy images of primary MucilAir-CF cell monolayers treated or not with TMA (200 nM) for 24 hrs are shown. In cells treated with solvent F508del CFTR was not expressed in the apical membrane, whereas after 200 nM TMA, F508del CFTR was significantly translocated to the apical membrane (ap, location of apical membrane bl, location of basolateral region. Scale bar, 10 μm). The results presented in FIG. 4 strongly confirm that TMA is a corrector of the mutated F508del CFTR protein non only in immortalised human bronchial epithelial cell lines but also in primary cells derived from the lung of a patient affected by cystic fibrosis.

REFERENCES

1) Welsh J M, Ramsey B W, Accurso F, Cutting G R. Cystic Fibrosis in "The Metabolic and Molecular Bases of Inherited Diseases". Scriver C R, Beaudet A L, Sly W S, Valle D (Eds) McGraw-Hill, New York, 2001.
2) Jones A M, Helm J M. Emerging treatments in cystic fibrosis. Drugs. 69:1903-10, 2009.
3) Becq F, Mall M A, Sheppard D N, Conese M, Zegarra-Moran O. Pharmacological therapy for cystic fibrosis: from bench to bedside. J Cyst Fibros. 10:S129-45, 2011.
4) Van Goor F, Hadida S, Grootenhuis P D, Burton B, Cao D, Neuberger T, Turnbull A, Singh A, Joubran J, Hazlewood A, Zhou J, McCartney J, Arumugam V, Decker C, Yang J, Young C, Olson E R, Wine J J, Frizzell R A, Ashlock M, Negulescu P. Rescue of CF airway epithelial cell function in vitro by a CFTR potentiator, VX-770. Proc Natl Acad Sci USA. 106:18825-30, 2009.
5) Accurso F J, Rowe S M, Clancy J P, Boyle M P, Dunitz J M, Durie P R, Sagel S D, Hornick D B, Konstan M W, Donaldson S H, Moss R B, Pilewski J M, Rubenstein R C, Uluer A Z, Aitken M L, Freedman S D, Rose L M, Mayer-Hamblett N, Dong Q, Zha J, Stone A J, Olson E R, Ordo√±ez C L, Campbell P W, Ashlock M A, Ramsey B W. Effect of VX-770 in persons with cystic fibrosis and the G551D-CFTR mutation. N Engl J Med. 363:1991-2003, 2010.

6) Flume P A, Liou T G, Borowitz D S, Li H, Yen K, Ordonez C L, Geller D E; for the VX08-770-104 Study Group. Ivacaftor in Subjects with Cystic Fibrosis who are Homozygous for the F508del-CFTR Mutation. Chest. 2012 Sep; 142(3):718-24.

7) Van Goor F, Hadida S, Grootenhuis P D, Burton B, Stack J H, Straley K S, Decker C J, Miller M, McCartney J, Olson E R, Wine J J, Frizzell R A, Ashlock M, Negulescu P A. Correction of the F508del-CFTR protein processing defect in vitro by the investigational drug VX-809. Proc Natl Acad Sci USA. 108:18843-8, 2011.

8) Clancy J P, Rowe S M, Accurso F J, Aitken M L, Amin R S, Ashlock M A, Ballmann M, Boyle M P, Bronsveld I, Campbell P W, De Boeck K, Donaldson S H, Dorkin H L, Dunitz J M, Durie P R, Jain M, Leonard A, McCoy K S, Moss R B, Pilewski J M, Rosenbluth D B, Rubenstein R C, Schechter M S, Botfield M, Ordonez C L, Spencer-Green G T, Vernillet L, Wisseh S, Yen K, Konstan M W. Results of a phase IIa study of VX-809, an investigational CFTR corrector compound, in subjects with cystic fibrosis homozygous for the F508del-CFTR mutation. Thorax. 67:12-8, 2011.

9) www.clinicaltrials.gov Study of VX-809 Alone and in Combination With VX-770 in Cystic Fibrosis (CF) Patients Homozygous or Heterozygous for the F508del-CFTR Mutation, NCT01225211.

10) Tamanini A, Borgatti M, Finotti A, Piccagli L, Bezzerri V, Favia M, Guerra L, Lampronti I, Bianchi N, Dall'acqua F, Vedaldi D, Salvador A, Fabbri E, Mancini I, Nicolis E, Casavola V, Cabrini G, Gambari R. Trimethylangelicin Reduces IL-8 Transcription and Potentiates CFTR Function. Am J Physiol Lung Cell Mol Physiol. 300: L380-90, 2011.

11) Piccagli L, Borgatti M, Nicolis E, Bianchi N, Mancini I, Lampronti I, Vevaldi D, Dall'Acqua F, Cabrini G, Gambari R. Virtual screening against nuclear factor kB (NF-kB) of a focus library: Identification of bioactive furocoumarin derivatives inhibiting NF-kB dependent biological functions involved in cystic fibrosis. Bioorg Med Chem. 18:8341-9, 2010.

12) Zeitlin P L, Lu L, Rhim J, Cutting G, Stetten G, Kieffer K A, Craig R, Guggino W B. A cystic fibrosis bronchial epithelial cell line: immortalisation by adeno-12-SV40 infection. Am J Respir Cell Mol Biol. 4:313-9, 1991.

13) Stern R S. Psoralen and ultraviolet a light therapy for psoriasis. N Engl J Med. 357:682-90, 2007.

14) Kong L D, Tan R X, Woo A Y, Cheng C H. Inhibition of rat brain monoamine oxidase activities by psoralen and isopsoralen: implications for the treatment of affective disorders. Pharmacol Toxicol. 88:75-80, 2001.

15) Mosti L, Lo Presti E, Menozzi G, Marzano C, Baccichetti F, Falcone G, Filippelli W, Piucci B. Synthesis of angelicin heteroanalogues: preliminary photobiological and pharmacological studies. Farmaco. 53:602-10, 1998.

16) Sardari S, Mori Y, Horita K, Micetich R G, Nishibe S, Daneshtalab M. Synthesis and antifungal activity of coumarins and angular furanocoumarins. Bioorg Med Chem. 7:1933-40, 1999.

17) Jakobs A E, Christiaens L. A Convenient Synthesis of Thiopyrano[2,3-e]benzofuran: A New Sulfur Analogue of Angelicin. J Org Chem. 61:4842-4844, 1996.

18) Iester M, Fossa P, Menozzi G, Mosti L, Baccichetti F, Marzano C, Simonato M. Synthesis and photobiological properties of 3-acylangelicins, 3-alkoxycarbonylangelicins and related derivatives. Farmaco 50:669-78, 1995.

19) Bisagni E. Synthesis of psoralens and analogues. J Photochem Photobiol B. 14:23-46, 1992.

20) Dall'Acqua F, Vedaldi D, Bordin F, Baccichetti F, Carlassare F, Tamaro M, Rodighiero P, Pastorini G, Guiotto A, Recchia G, Cristofolini M. 4'-Methylangelicins: new potential agents for the photochemotherapy of psoriasis. J Med Chem. 26:870-6, 1983.

21) Dall'Acqua F, Vedaldi D, Guiotto A, Rodighiero P, Carlassare F, Baccichetti F, Bordin F. Methylangelicins: new potential agents for the photochemotherapy of psoriasis. Structure-activity study on the dark and photochemical interactions with DNA. J Med Chem. 24:806-11, 1981.

22) Conconi M T, Montesi F, Parnigotto P P. Antiproliferative activity and phototoxicity of some methyl derivatives of 5-methoxypsoralen and 5-methoxyangelicin. Pharmacol Toxicol. 82:193-8, 1998.

23) Marzano C, Severin E, Pani B, Guiotto A, Bordin F. DNA damage and cytotoxicity induced in mammalian cells by a tetramethylfuroquinolinone derivative. Environ Mol Mutagen. 29:256-64, 1997.

24) Bordin F, Dall'Acqua F, Guiotto A. Angelicins, angular analogs of psoralens: chemistry, photochemical, photobiological and phototherapeutic properties. Pharmacol Ther. 52:331-63, 1991.

25) Guerra L, Fanelli T, Favia M, Riccardi S M, Busco G, Cardone R A, Carrabino S, Weinman E J, Reshkin S J, Conese M, Casavola V. Na+/H+ exchanger regulatory factor isoform 1 overexpression modulates cystic fibrosis transmembrane conductance regulator (CFTR) expression and activity in human airway 16HBE14o− cells and rescues DeltaF508 CFTR functional expression in cystic fibrosis cells. J Biol Chem. 280:40925-33, 2005.

26) Favia M, Guerra L, Fanelli T, Cardone R A, Monterisi S, Di Sole F, Castellani S, Chen M, Seidler U, Reshkin S J, Conese M, Casavola V. Na+/H+ exchanger regulatory factor 1 overexpression-dependent increase of cytoskeleton organisation is fundamental in the rescue of F508del cystic fibrosis transmembrane conductance regulator in human airway CFBE41o− cells. Mol Biol Cell. 21:73-86, 2010.

27) Ma T, Thiagarajah J R, Yang H, Sonawane N D, Folli C, Galietta L J, Verkman A S. Thiazolidinone CFTR inhibitor identified by high-throughput screening blocks cholera toxin-induced intestinal fluid secretion. J Clin Invest. 110: 1651-8, 2002.

28) Neuberger T, Burton B, Clark H, Van Goor F. Use of primary cultures of human bronchial epithelial cells isolated from cystic fibrosis patients for the pre-clinical testing of CFTR modulators. Methods Mol Biol. 741:39-54, 2011.

29) Pedemonte N, Tomati V, Sondo E, Galietta L J. Influence of cell background on pharmacological rescue of mutant CFTR. Am J Physiol Cell Physiol. 298:C866-74, 2010.

The invention claimed is:

1. A method of correcting CFTR in patients suffering from cystic fibrosis and carrying mutation F508del-CFTR, either in heterozygous or homozygous state, said method comprising:

administering an effective amount of a CFTR corrector to said patients suffering from cystic fibrosis and carrying said mutation F508del-CFTR either in heterozygous or homozygous state; and correcting said CFTR in said patients, wherein said CFTR corrector is trimethylangelicin.

2. The method according to claim 1, wherein said effective amount is approximately from 10 mg to approximately 500 mg a day.

* * * * *